(12) United States Patent
Eggleston et al.

(10) Patent No.: US 11,579,070 B2
(45) Date of Patent: Feb. 14, 2023

(54) FUNCTIONALISED PARTICLES

(71) Applicant: Nokia Technologies Oy, Espoo (FI)

(72) Inventors: Michael Eggleston, Murray Hill, NJ (US); Shreyas Shah, Dayton, NJ (US)

(73) Assignee: Nokia Technologies Oy, Espoo (FI)

( * ) Notice: Subject to any disclaimer, the term of this patent is extended or adjusted under 35 U.S.C. 154(b) by 339 days.

(21) Appl. No.: 16/645,696

(22) PCT Filed: Sep. 14, 2018

(86) PCT No.: PCT/FI2018/050669
§ 371 (c)(1),
(2) Date: Mar. 9, 2020

(87) PCT Pub. No.: WO2019/058026
PCT Pub. Date: Mar. 28, 2019

(65) Prior Publication Data
US 2020/0264090 A1    Aug. 20, 2020

(30) Foreign Application Priority Data
Sep. 22, 2017 (EP) .................................. 17192589

(51) Int. Cl.
| *G01N 15/14* | (2006.01) |
|---|---|
| *G01N 21/75* | (2006.01) |
| *G01N 33/543* | (2006.01) |
| *C07K 16/44* | (2006.01) |
| *C12Q 1/6804* | (2018.01) |
| *G01N 15/00* | (2006.01) |

(52) U.S. Cl.
CPC ......... *G01N 15/1434* (2013.01); *C07K 16/44* (2013.01); *C12Q 1/6804* (2013.01); *G01N 21/75* (2013.01); *G01N 33/54313* (2013.01); *G01N 2015/0038* (2013.01); *G01N 2015/0065* (2013.01)

(58) Field of Classification Search
CPC ............... G01N 15/1434; G01N 21/75; G01N 2015/0038; G01N 33/54313; G01N 2015/0065; C07K 16/44; C12Q 1/6804
USPC ....................................................... 435/6.19
See application file for complete search history.

(56) References Cited

U.S. PATENT DOCUMENTS

| 5,982,959 A | 11/1999 | Hopenfeld ..................... 385/12 |
|---|---|---|
| 6,165,389 A | 12/2000 | Asher et al. |
| 9,274,105 B2 * | 3/2016 | Guo ................. G01N 33/54346 |

(Continued)

FOREIGN PATENT DOCUMENTS

| CN | 100581458 C | 1/2010 |
|---|---|---|
| EP | 2500314 A1 | 9/2012 |

(Continued)

OTHER PUBLICATIONS

Office action received for corresponding European Patent Application No. 17192589.4, dated Jul. 16, 2020, 6 pages.

(Continued)

*Primary Examiner* — Tarifur R Chowdhury
*Assistant Examiner* — Omar H Nixon
(74) *Attorney, Agent, or Firm* — Harrington & Smith (57) ABSTRACT

A functionalised particle, wherein the particle has a first optical spectral signature in a first structural configuration of the particle and a second optical spectral signature in a second structural configuration of the particle.

20 Claims, 5 Drawing Sheets

(56) References Cited

U.S. PATENT DOCUMENTS

| | | | |
|---|---|---|---|
| 2005/0171433 A1 | 8/2005 | Boppart et al. | |
| 2006/0285635 A1 | 12/2006 | Boppart et al. | |
| 2007/0009968 A1* | 1/2007 | Cunningham | G02B 6/1225 |
| | | | 435/7.9 |
| 2007/0188749 A1 | 8/2007 | Brady et al. | |
| 2009/0304591 A1 | 12/2009 | Russmann et al. | 424/9.1 |
| 2012/0237605 A1 | 9/2012 | Messersmith et al. | |
| 2013/0115717 A1* | 5/2013 | Guo | G01N 33/54346 |
| | | | 422/69 |
| 2016/0153975 A1 | 6/2016 | Biris et al. | |

FOREIGN PATENT DOCUMENTS

| | | | | |
|---|---|---|---|---|
| JP | 2009269998 A | 11/2009 | | |
| JP | 2013-522653 A | 6/2013 | | |
| WO | 01/55704 A1 | 8/2001 | | |
| WO | 02/01228 A2 | 1/2002 | | |
| WO | 2004/042403 A2 | 5/2004 | | |
| WO | 2008/018933 A2 | 2/2008 | | |
| WO | 2011/119822 A1 | 9/2011 | | |
| WO | WO-2012083027 A1 * | 6/2012 | | G01N 21/658 |
| WO | WO-2012/160364 A1 | 11/2012 | | |

OTHER PUBLICATIONS

Office action received for corresponding Japanese Patent Application No. 2020-515744, dated Jun. 6, 2022, 4 pages of office action and 4 pages of translation available.

Stevens et al., "Characterization of glucose responsive phenylboronic acid-based hydrogel using optical coherence tomography", Sensors, Nov. 2-5, 2014, 4 pages.

Shah et al., Microparticle-Based Biochemcal Sensing Using Optical Coherence Tomography and Deep Learning, ACS Nano, vol. 15, No. 6, 2020, pp. 1-25.

Wang et al., "Detection and Monitoring of Microparticles Under Skin by Optical Coherence Tomography as an Approach to Continuous Glucose Sensing Using Implanted Retroreflectors", IEEE Sensors Journal, vol. 13, No. 11, Nov. 2013, pp. 4534-4541.

Kim et al., "Enhanced detection of early-stage oral cancer in vivo by optical coherence tomography using multimodal delivery of gold nanoparticles", Journal of Biomedical Optics, vol. 14, No. 3, 2009, pp. 1-17.

Au et al., "Polypyrrole Nanoparticles: A Potential Optical Coherence Tomography Contrast Agent for Cancer Imaging", Advanced Materials, vol. 23, No. 48, Dec. 22, 2011, pp. 5792-5795.

Schwartz et al., "In vivo imaging of nanoparticle delivery and tumor microvasculature with multimodal optical coherence tomography", Biomedical Optics Express, vol. 5, No. 6, Jun. 2014, pp. 1731-1743.

Kim et al., "Droplet Microfluidics for Producing Functional Microparticles", Langmuir, vol. 30, No. 6, 2014, pp. 1473-1488.

Ouiganon et al., "An application of optical coherence tomography and a smart polymer gel to construct an enzyme-free sugar sensor", Applied Physics B, vol. 122, No. 6, 2016, pp. 1-8.

Xu et al., "Wavelength-dependent scattering in spectroscopic optical coherence tomography", Optics Express, vol. 13, No. 14, Jul. 11, 2005, pp. 5450-5462.

Partial European Search Report received for corresponding European Patent Application No. 17192589.4, dated Feb. 22, 2018, 9 pages.

Extended European Search Report received for corresponding European Application No. 17192589.4, dated Jun. 8, 2018, 15 pages.

International Search Report and Written Opinion received for corresponding Patent Cooperation Treaty Application No. PCT/FI2018/050669, dated Dec. 17, 2018, 20 pages.

\* cited by examiner

FUNCTIONALISED PARTICLES

RELATED APPLICATION

This application claims priority to PCT Application No. PCT/FI2018/050669 filed Sep. 14, 2018, which claims priority to EP Patent Application No. 17192589.4, filed on Sep. 22, 2017, each of which is incorporated herein by reference in its entirety.

TECHNICAL FIELD

Aspects relate, in general, to functionalised particles and methods for use thereof.

BACKGROUND

Biosensing can be used in as part of health monitoring and medical diagnosis, and is typically performed in vitro on samples taken from the body. For example, a probing/sensing element and a transducing element can be used to generate a measurable signal in response to a biological interaction that occurs when a sample interacts with the sensing element.

SUMMARY

According to an example, there is provided a functionalised particle, wherein the particle has a first optical spectral signature in a first structural configuration of the particle and a second optical spectral signature in a second structural configuration of the particle. The particle can comprise a dielectric core and a dielectric coating around the core. Various other materials may be used for one, other or both of the particle core and coating, examples of which are described below. For example, a polymeric material such as a polymeric dielectric material can be used for either or both of a core and coating.

In an example, the first structural configuration of the particle comprises the core and coating and the second structural configuration of the particle comprises the core without the coating. Alternatively, the first structural configuration of the particle comprises the particle in an un-swollen or swollen state and the second structural configuration of the particle comprises the particle in a corresponding swollen or un-swollen state. Alternatively, the first structural configuration of the particle comprises the core and coating and the second structural configuration of the particle comprises the core with a modified coating. The coating (modified, swollen, un-swollen, degraded and so on) causes a change in the refractive index, absorption or polarisation of the particle, thereby leading to a change in the optical spectrum of the particle. That is, in an example, the particle has respective different refractive indices, absorptions or polarisations in the first and second structural configurations.

According to an example, there is provided a method for detecting a change in an optical spectral signature of a functionalised particle, the method comprising providing a particle with a first optical spectral signature, detecting the first optical spectral signature using spectroscopic optical coherence tomography, and tracking a change from the first optical spectral signature to a second optical spectral signature of the particle in the presence of a material which recognises, binds to, has affinity for or modifies the particle. Detecting a change can include detecting a change in one or more of the refractive index, absorption and polarisation of the particle. The method can comprise coating a particle core with a second material configured to degrade in the presence of the material. The particle core and coating can be dielectric materials. In an example, the method is performed in vivo or in vitro.

According to an example, there is provided a method for aiding diagnosis or prognostic monitoring in a subject, said method comprising providing a particle with a first optical spectral signature, detecting the first optical spectral signature in the subject using spectroscopic optical coherence tomography, and tracking a change from the first optical spectral signature to a second optical spectral signature of the particle in the presence of a material which recognises, binds to, has affinity for or modifies the particle.

According to an example, there is provided use for diagnostic or prognostic applications of a functionalised particle, wherein the particle has a first optical spectral signature in a first structural configuration of the particle and a second optical spectral signature in a second structural configuration of the particle in the presence of a material which recognises, binds to, has affinity for or modifies the particle. The material can be a biomarker, enzyme, protein, carbohydrate, small molecule drug or nucleic acid, the presence of which provokes a change in the refractive index, absorption or polarisation of the functionalised particle.

According to an example, there is provided a kit for use in diagnostic or prognostic applications, comprising a functionalised particle, wherein the particle has a first optical spectral signature in a first structural configuration of the particle and a second optical spectral signature in a second structural configuration of the particle, and spectroscopic optical coherence tomography apparatus configured to track or detect a change from the first optical spectral signature to a second optical spectral signature of the particle.

BRIEF DESCRIPTION OF THE DRAWINGS

Embodiments will now be described, by way of example only, with reference to the accompanying drawings, in which.

DESCRIPTION

Example embodiments are described below in sufficient detail to enable those of ordinary skill in the art to embody and implement the systems and processes herein described. It is important to understand that embodiments can be provided in many alternate forms and should not be construed as limited to the examples set forth herein.

Accordingly, while embodiments can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

The terminology used herein to describe embodiments is not intended to limit the scope. The articles "a," "an," and "the" are singular in that they have a single referent, however the use of the singular form in the present document should not preclude the presence of more than one referent. In other words, elements referred to in the singular can number one or more, unless the context clearly indicates otherwise. It will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof.

Unless otherwise defined, all terms (including technical and scientific terms) used herein are to be interpreted as is customary in the art. It will be further understood that terms in common usage should also be interpreted as is customary in the relevant art and not in an idealized or overly formal sense unless expressly so defined herein.

Currently, detecting the presence of specific biomarkers can be performed by taking samples from a patient (e.g. blood, urine, biopsy, etc.) and analyzing those samples in a laboratory. Conventional methods for detecting a specific biomarker rely on stringent microbiological and biochemical analyses, the most popular being ELISA (enzyme-linked immunosorbent assay) and PCR (polymerase chain reaction). However, these methods are time-consuming, labor-intensive, costly due to expensive reagents as well as instrumentation, and require carefully trained personal.

Compared to such conventional biochemical-based methods, biosensors are more portable and cost-effective, and require less sample preparation and reagents. However, these devices are used outside of the body, due to their relatively large size (at least millimeter to centimeter scale) and biologically-incompatible packaging. They also tend to require wiring to external instrumentation to acquire the measurement of signals, and at best allow for intermittent monitoring.

According to an example, there is provided a non-invasive method for monitoring biomarkers in the body on a continuous basis. Functionalized particles possessing a tuneable optical signature can be detected using an optical coherence tomography (OCT)-based monitoring system, thereby enabling remote biosensing to be performed in vivo.

Traditional OCT is capable of detecting structural information in a 3D volume. Spectroscopic OCT is a functional imaging method that uses wideband wavelength information inherent to an OCT system to extract spectroscopic information from the target being imaged. It has been mainly used with nanoparticle tags as a substitute for fluorescent tags in OCT imaging where metallic nanoparticles with distinct resonance peaks are functionalized to "stick" to a target bio-molecule. Over time, these nanoparticles form large aggregations around the bio-molecule of interest because they get "stuck" to it. By using spectroscopic OCT, these regions with large aggregations are easily identifiable because the nanoparticles have a distinct spectral resonance that gives enhanced contrast in the OCT image. This effectively works like staining, where particular bio-molecules are highlighted. It does not, however, work as any sort of biosensor, since the functionalized nanoparticles exist in the sample regardless of whether there is any target bio-molecule there and is similar to other OCT methods that rely on aggregation of nanoparticles to increase contrast in the OCT images. In addition, it only works for clustered bio-molecules because if the bio-molecules are evenly distributed in a tissue (like glucose is in blood and interstitial fluid for example) the functionalized nano-particles would also be evenly distributed and the measured signal would look identical to the signal if the target bio-molecule was not there.

According to an example, a particle can be used in the body (e.g. placed via skin through a topical cream, oral ingestion, or injection into the blood stream, etc.) that has a specific optical signature (such as scattering and/or absorption). The optical signature of the particle can be tailored to change in the presence of a biomarker, and this change in optical spectral signature can be detected, in the body, using spectroscopic OCT, which would be located outside of the body, but is capable of imaging up to several centimeters into the body. This does not rely on an aggregation of large numbers of nanoparticles to do in vivo OCT detection. Rather, there is a modification or breakdown of a single resonant particle, which enables less particles used and enables multiplexed detection.

According to an example, a functionalised particle has a first optical spectral signature in a first structural configuration of the particle and a second optical spectral signature in a second structural configuration of the particle. Accordingly, a change in the structural configuration of the particle will lead to a change in its optical characteristics, which change can be tracked or determined.

Figure 1:
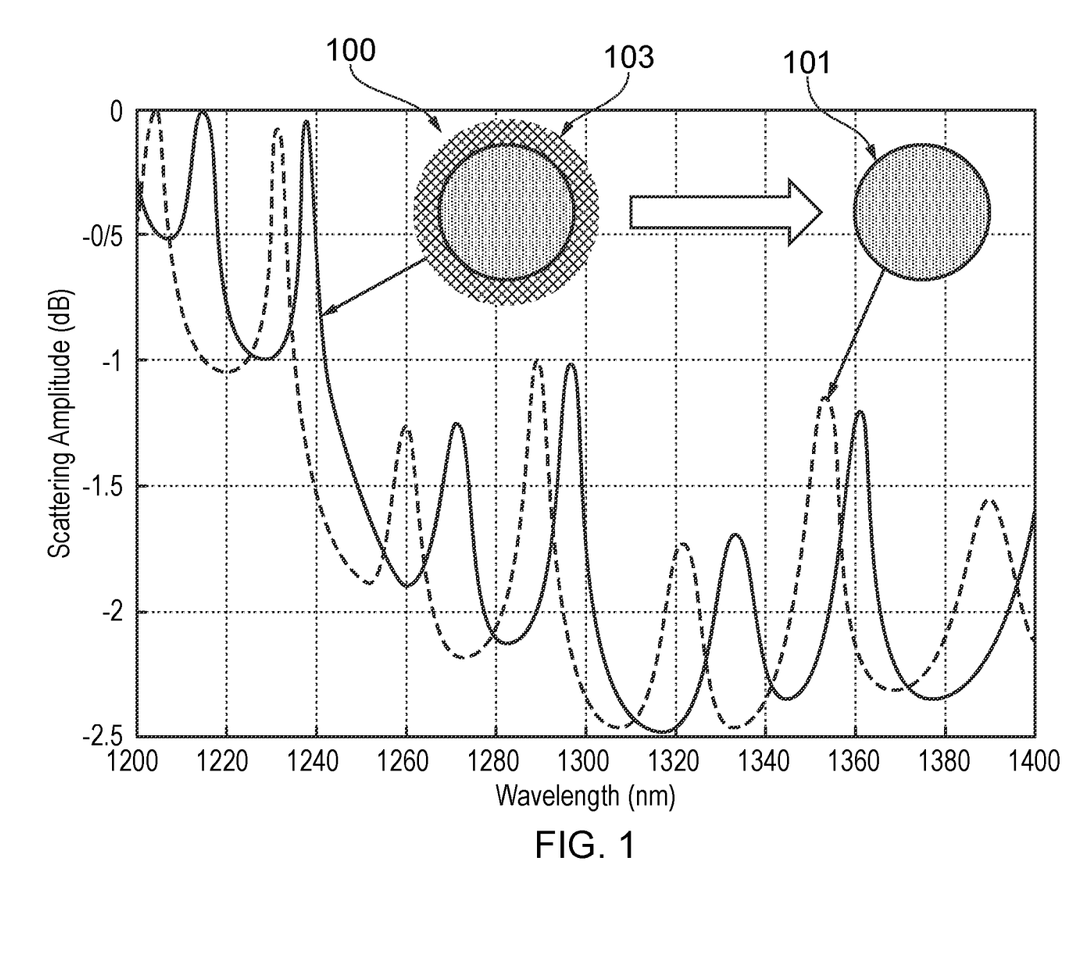
FIG. 1 is a schematic representation of the scattering amplitude of a high-dielectric (refractive index, n=1.9) sphere with a diameter of 5 μm according to an example.
Figure 5:
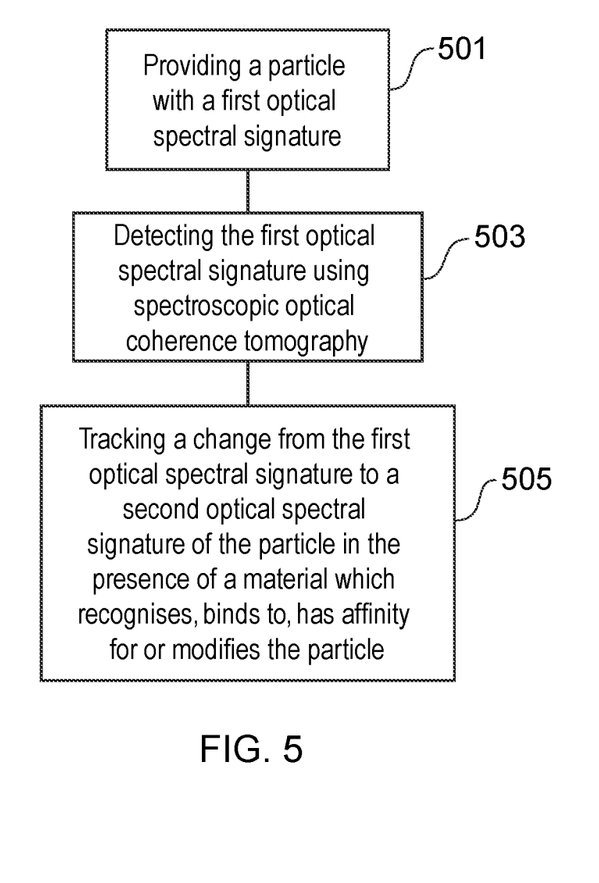
FIG. 5 is a flowchart of a method according to an example.

FIG. 1 is a schematic representation of the scattering amplitude of a high-dielectric (refractive index, n=1.9) sphere with a diameter of 5 μm according to an example. In the example of FIG. 5, a functionalized particle 100 comprises a dielectric core 101 (n=1.9) coated with a thin material 103 (n=1.45). The particle 100 has a first optical spectral signature in a first structural configuration of the particle, in which the particle comprises the core 101 and coating 103, and a second optical spectral signature in a second structural configuration of the particle in which the coating 103 is degraded or otherwise not present leaving just the core 101. That is, in the example of FIG. 1, the first optical signature relates to a first refractive index of the particle 100 where n=1.45, and the second optical signature of the particle relates to the second refractive index of the particle 101 where n=1.9 (i.e. no coating present).

Thus, when the coating 103 is removed or otherwise degraded or not present the scattering spectrum of the particle 100 red-shifts. The shift in the scattering spectrum is depicted in FIG. 1 where the scattering spectrum for the particle 100 is shown both with and without the coating present.

In an example, the coating 103, or shell, of the particle 100 can be functionalized to degrade in the presence of another material, such as a biomarker for example. In the presence of such a material, the coating 103 will therefore degrade causing the optical characteristics of the particle 100 to change and thus the subsequent scattering spectra would change.

As the change in particle size is small, conventional OCT methods would not be able to distinguish any change. However, according to an example, by tracking the optical spectrum of the particle 100 with spectroscopic OCT, the small structural change can be detected by a much more pronounced spectral change, as depicted in FIG. 1 for example.

According to an example, a particle core and particle coating can be made from a variety of natural and synthetic materials. Below are some examples:

Natural materials—chitosan, collagen, alginate, dextran, gelatin, and albumin.

Synthetic materials (usually polymeric in nature)—polystyrene, polyacrylamide, polymethylmethacrylate [PMMA], polyethylene glycol [PEG], poly(lactic acid) [PLA], poly(glycolic acid) [PGA], poly(lactide-co-glycolic acid) [PLGA], Poly(N-isopropylacrylamide) [pNIPAM], poly(ε-caprolactone) [PCL], and poly(3-hydroxybutyrate-co-3-hydroxyvalerate) [PHBV].

Other types of materials (which would generally be used just as a core)—glass, titania, ceramic, silica, magnetic, and metallic (gold, silver).

According to an example, functionalised particles can be injected into the skin or placed under the skin through the use of a topical cream so that they then diffuse the dermis layer which is soaked in the interstitial fluid. In an example, the properties of the outer shell layer of a particle can be engineered or configured to change in response to a specific biomarker or biochemical cue. This optical change (i.e. providing the shift from a first to a second optical spectral signature) can alternatively be caused by swelling or degrading of a particle, which may be reversible, thereby changing the refractive index of the particle, or changing the material absorption spectra through a chemical change in the particle. That is, a change from a first to a second structural configuration of the particle (and vice-versa) can be by removal or degradation of a coating or swelling/deswelling. In an example, a combination of the two structural configurations can be used. That is, a particle can comprise a coating that degrades in the presence of a first material and core that swells in the presence of a second material.

Accordingly, when a particle comes into contact with a specific biomolecule (e.g. cancer marker), the outer shell can degrade and the subsequent change in optical property can be detected remotely using spectroscopic-OCT. The OCT system could either be a tabletop or an integrated wearable device located outside the body.

Figure 2:
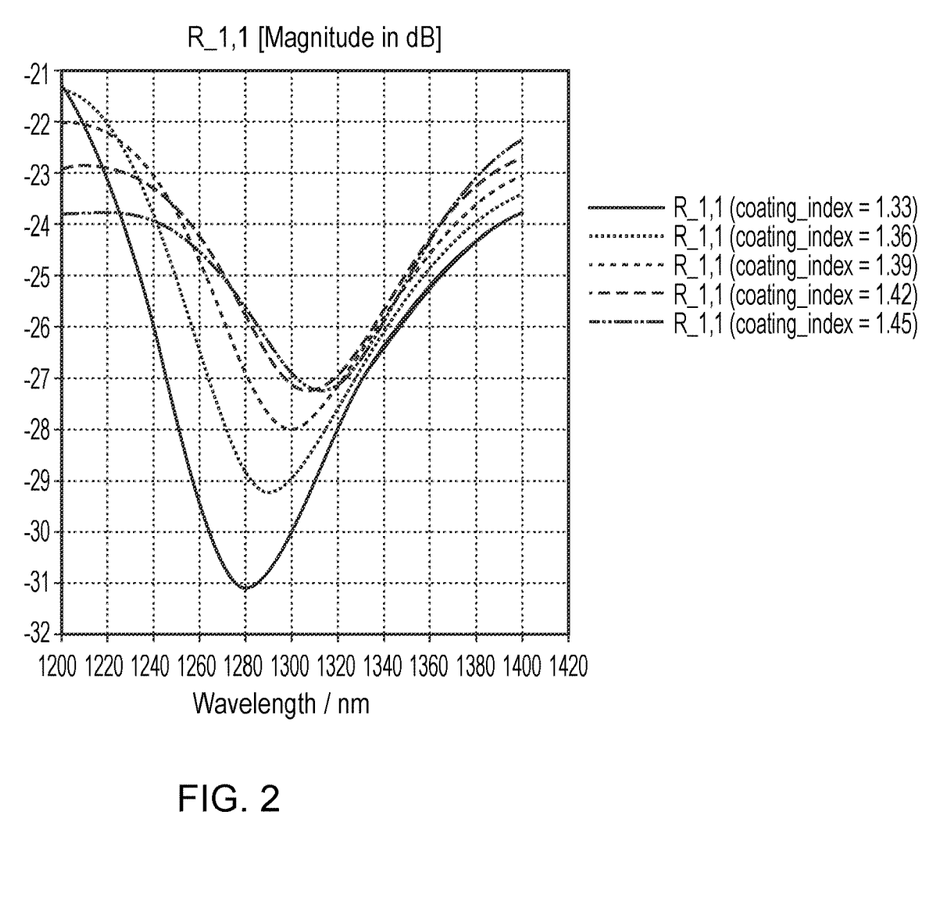
FIG. 2 is a schematic representation of the scattering spectrum of a gold nanorod that has been coated with a 100 nm dielectric coating according to an example.

Instead of degrading, a particle can be coated in a material that is functionalized to change refractive index in the presence of a certain biomarker. FIG. 2 is a schematic representation of the scattering spectrum of a gold nanorod that has been coated with a 100 nm dielectric coating according to an example. As the dielectric coating changes refractive index, the scattering resonance of the gold nanoparticle also changes. If the coating is functionalized to change refractive index proportional to, for example, a surrounding glucose concentration, then the particle could be injected into the blood stream or placed in the dermis layer of the skin. The scattering spectra of the gold nanorod could then be detected with spectroscopic OCT to determine the blood glucose level in vivo. Since the total scattering from the particle remains relatively constant, there would be no observable change using traditional OCT methods. However, if spectroscopic OCT is employed, this shift in peak optical resonance could be detected. In the example of FIG. 2, the gold nanorod is 30 nm in diameter and 175 nm long and coated in a 100 nm thick dielectric material. The scattering spectrum of the gold nanorod is depicted (right hand side of FIG. 2) as the dielectric constant of the dielectric coating changes from 1.33 to 1.45.

Figure 3:
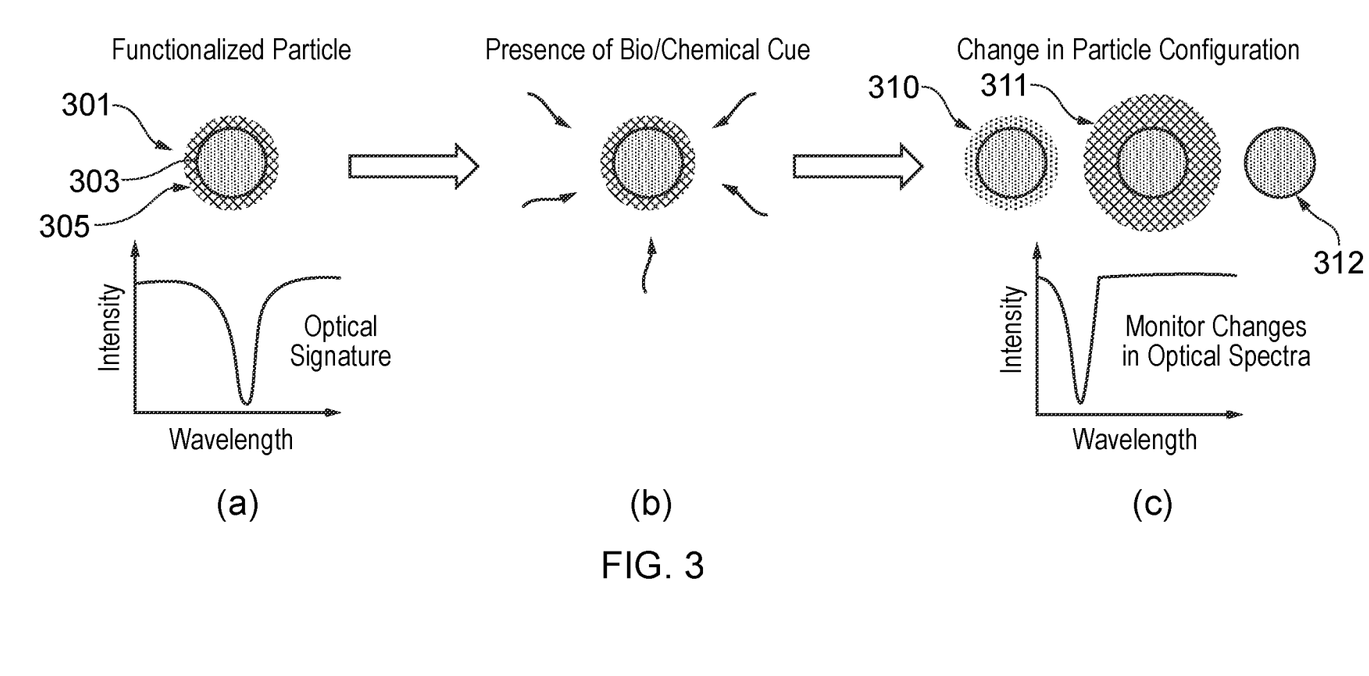
FIG. 3 is a schematic representation depicting a change in an optical spectral signature of a functionalised particle according to an example.

FIG. 3 is a schematic representation depicting a change in an optical spectral signature of a functionalised particle according to an example. FIG. 3a depicts the optical signature of a particle 301, the particle comprising a core 303 and coating 305. In FIG. 3b, the particle 301 is exposed to a biological or chemical cue that affects the coating 305 in a predictable way. That is, the coating 305 is configured to react to the presence of the biological or chemical cue. The result of the exposure to the biological or chemical cue is depicted in FIG. 3c, in which the coating 305 is modified, thereby altering the optical spectrum of the particle. In the example of FIG. 3c, several potential changes to the particle coating are depicted—the coating can be modified (310) in the presence of the biological or chemical cue thereby resulting in a change to the refractive index, absorption or polarisation of the particle, the coating may swell (311) or conversely may reduce in size, or the coating may degrade (312). The degradation may be significant to the extent that the coating is no longer present on the core of the particle.

Figure 4:
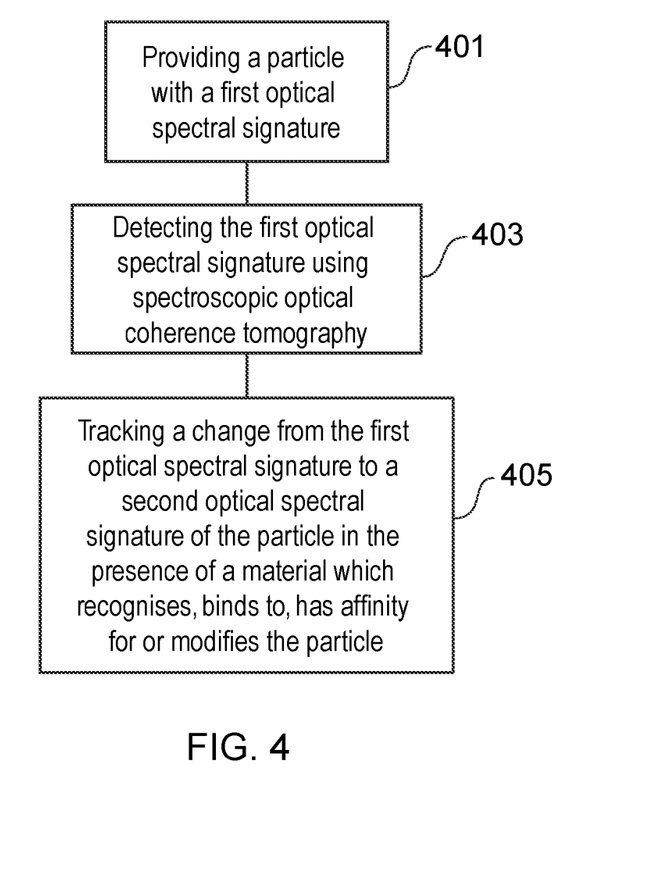
FIG. 4 is a flowchart of a method according to an example.

FIG. 4 is a flowchart of a method according to an example. More specifically, FIG. 4 is a flow chart of a method for detecting a change in an optical spectral signature of a functionalised particle according to an example. In block 401 a particle with a first optical spectral signature is provided. The first optical spectral signature is defined by a first structural configuration of the particle. This first structural configuration can be provided by the size of the particle (e.g. it is in a swollen or un-swollen state) or by way of a coating as described above for example. In block 403 the first optical spectral signature is detected using spectroscopic optical coherence tomography. This can be performed in vivo or in vitro. In block 405 a change from the first optical spectral signature to a second optical spectral signature of the particle in the presence of a material which recognises, binds to, has affinity for or modifies the particle is tracked. That is, a change of optical spectral signature of the particle is detected.

FIG. 5 is a flowchart of a method according to an example. More specifically, FIG. 5 is a flowchart of a method for aiding diagnosis or prognostic monitoring according to an example. In block 501 a particle with a first optical spectral signature is provided. The first optical spectral signature is defined by a first structural configuration of the particle. This first structural configuration can be provided by the size of the particle (e.g. it is in a swollen or un-swollen state) or by way of a coating as described above for example. In block 503 the first optical spectral signature is detected using spectroscopic optical coherence tomography. This can be performed in vivo or in vitro. In block 505 a change from the first optical spectral signature to a second optical spectral signature of the particle in the presence of a material which recognises, binds to, has affinity for or modifies the particle is tracked. That is, a change of optical spectral signature of the particle is detected.

According to an example, particles that are functionalized to change in the presence of a specific stimuli/biomarker can be made in a number of ways. For example, enzyme-cleavable peptides can be incorporated into the backbone of a polymeric particle to facilitate degradation in the presence of specific enzymes.

The expression and activity of enzymes is known to be altered in association with cancer, disease, inflammation, or pathological disorders. Thus, in an example, particles can be tailored to have recognition elements (e.g. peptide chains/linkers, polymer-peptide conjugates) that are specifically recognized by associated proteolytic enzymes (e.g. matrix metalloproteinase, MMPs). The subsequent interaction of the enzyme with the peptide-based recognition element leads to cleavage of the peptide, in turn leading to degradation of the overall particle thereby altering its optical spectral signature.

In another example, small molecule-based recognition elements can be incorporated into a particle backbone to facilitate swelling/deswelling in the presence of biochemicals. In this example, the binding of a target biochemical to the recognition element alters the charge distribution or hydrophobic/hydrophilic interactions within the polymeric particle, leading to osmotic swelling/deswelling. For example, glucose binding to phenylboronic acid-derivatives which are covalently-bound to a polymeric backbone of a particle.

According to an example, utilizing spectroscopic OCT to identify and monitor the unique optical signature of a functionalized particle enables in-body biosensing and continuous monitoring. As described above, a particle size, shape and composition defines the dielectric particle's optical properties, which can be further modulated by changing the surface properties. The variety of chemical functionalization can be used to make the surface responsive to specific analytes in the surrounding environment, giving rise to a versatile in vivo sensor for remote biosensing.

As used herein, a functionalized particle refers to a particle or other small localized object which has a surface that has been functionalized for a specific application. The functionalization includes surface modification of the particle—that is, a particle includes a core and a coating, and the coating (at least) can be geared to react in the presence of a specific biomarker, as described above. In another example, as described above, the functionalization of the particle can be such that the particle, as a whole (as opposed to just a coating) can react in the presence of a biomarker. For example, as described above, a particle can swell/deswell, and this structural change may be limited to a coating or may occur over a particle as a whole, in which case the particle may be formed from a single material for example.

The present inventions can be embodied in other specific apparatus and/or methods. The described embodiments are to be considered in all respects as illustrative and not restrictive. In particular, the scope of the invention is indicated by the appended claims rather than by the description and figures herein. All changes that come within the meaning and range of equivalency of the claims are to be embraced within their scope. The term particle includes rod or string-like forms or formations and is not intended to be limited to spherical or other spheroid shapes.

The invention claimed is:

1. A functionalized particle, comprising:
   a first optical spectral signature in a first structural configuration of the particle; and
   a second optical spectral signature in a second structural configuration of the particle;
   wherein a modification of the second structural configuration of the particle comprises a degradation of a dielectric coating that causes an optical characteristic of the particle to change such that the change allows for a detection of a shift in a scattering spectrum of the particle.

2. A functionalized particle, as claimed in claim 1, wherein the particle comprises a dielectric core and a dielectric coating around the core.

3. A functionalized particle, as claimed in claim 2, wherein the first structural configuration of the particle comprises the core and coating and the second structural configuration of the particle comprises the core without the coating.

4. A functionalized particle, as claimed in claim 1, wherein the first structural configuration of the particle comprises the particle in an un-swollen or swollen state and the second structural configuration of the particle comprises the particle in a corresponding swollen or un-swollen state.

5. A functionalized particle, as claimed in claim 1, wherein the particle has respective different refractive indices, absorption or polarisations in the first and second structural configurations.

6. A functionalized particle as claimed in claim 1, wherein a change from the first optical spectral signature to the second optical spectral signature derives from a change in one or more of the refractive index, absorption and polarization of the particle between the first structural configuration and the second structural configuration.

7. A functionalized particle as claimed in claim 1, wherein the particle comprises a dielectric particle core coated with a second dielectric material configured to degrade in the presence of a material.

8. A method, the method comprising:
   providing a particle with a first optical spectral signature;
   detecting the first optical spectral signature using spectroscopic optical coherence tomography; and
   tracking a change from the first optical spectral signature to a second optical spectral signature of the particle in the presence of a material which recognizes, binds to, has affinity for, or modifies the particle;
   wherein the change to the second optical spectral signature comprises a degradation of a dielectric coating that causes an optical characteristic of the particle to change such that the change allows for a detection of a shift in a scattering spectrum of the particle.

9. A method as claimed in claim 8, further comprising;
   detecting a change in one or more of the refractive index, absorption and polarization of the particle.

10. A method as claimed in claim 8, wherein providing the particle comprises: coating a dielectric particle core with a second dielectric material configured to degrade in the presence of the material.

11. A method as claimed in claim 8 being used for aiding diagnosis or prognostic monitoring, said method comprising;
    providing a particle with a first optical spectral signature;
    detecting the first optical spectral signature in the subject using spectroscopic optical coherence tomography; and
    tracking a change from the first optical spectral signature to a second optical spectral signature of the particle in the presence of a material which recognizes, binds to, has affinity for or modifies the particle.

12. A method of claim 11, wherein during use for diagnostic or prognostic applications of a functionalized particle, the particle has a first optical spectral signature in a first structural configuration of the particle and a second optical spectral signature in a second structural configuration of the particle in the presence of a material which recognizes, binds to, has affinity for or modifies the particle.

13. A method of claim 12, wherein the material is a biomarker, enzyme, protein, carbohydrate, small molecule drug or nucleic acid, the presence of which provokes a change in the refractive index, absorption or polarization of the functionalized particle.

14. A kit for use in diagnostic or prognostic applications, comprising:
    a functionalized particle, wherein the particle has a first optical spectral signature in a first structural configuration of the particle and a second optical spectral signature in a second structural configuration of the particle; and spectroscopic optical coherence tomography apparatus configured to track or detect a change from the first optical spectral signature to a second optical spectral signature of the particle;

wherein a modification of the second structural configuration of the particle comprises a degradation of a dielectric coating that causes an optical characteristic of the particle to change such that the change allows for a detection of a shift in a scattering spectrum of the particle.

15. A kit as claimed in claim 14, wherein the particle comprises a dielectric core and a dielectric coating around the core.

16. A kit as claimed in claim 15, wherein the first structural configuration of the particle comprises the core and coating and the second structural configuration of the particle comprises the core without the coating.

17. A kit as claimed in claim 14, wherein the first structural configuration of the particle comprises the particle in an un-swollen or swollen state and the second structural configuration of the particle comprises the particle in a corresponding swollen or un-swollen state.

18. A kit as claimed in claim 14, wherein the particle has respective different refractive indices, absorption or polarizations in the first and second structural configurations.

19. A kit as claimed in claim 14, wherein a change from the first optical spectral signature to the second optical spectral signature derives from a change in one or more of the refractive index, absorption and polarization of the particle between the first structural configuration and the second structural configuration.

20. A kit as claimed in claim 14, wherein there particle comprises a dielectric particle core coated with a second dielectric material configured to degrade in the presence of the material.

* * * * *